US007355017B2

(12) United States Patent
Lofling et al.

(10) Patent No.: US 7,355,017 B2
(45) Date of Patent: Apr. 8, 2008

(54) BLOOD GROUP ANTIGEN FUSION POLYPEPTIDES AND METHODS OF USE THEREOF

(75) Inventors: Jonas Lofling, Alvsjo (SE); Jan Holgersson, Huddinge (SE)

(73) Assignee: Absorber AB, Stockholm (SE)

( * ) Notice: Subject to any disclaimer, the term of this patent is extended or adjusted under 35 U.S.C. 154(b) by 831 days.

(21) Appl. No.: 10/199,342

(22) Filed: Jul. 19, 2002

(65) Prior Publication Data
US 2003/0073822 A1    Apr. 17, 2003

Related U.S. Application Data

(60) Provisional application No. 60/306,984, filed on Jul. 20, 2001.

(51) Int. Cl.
    C07K 16/00 (2006.01)
(52) U.S. Cl. ............... 530/391.1; 530/391.7; 530/395; 530/402; 530/403; 530/866
(58) Field of Classification Search ......... 530/391.1, 530/391.7, 395, 402, 403, 866
    See application file for complete search history.

(56) References Cited

U.S. PATENT DOCUMENTS 6,943,239 B2* 9/2005 Holgersson et al. ........ 530/402

FOREIGN PATENT DOCUMENTS

WO    WO 98/42750    10/1998

OTHER PUBLICATIONS

Aeed, P.A., Geng. J.G., Asa, D., Raycroft, L., Ma, L., and Elhammer, A.P. (1998) Characterization of the 0-linked ollgosaccharide structures on P-selection glycoprotein ligand-I (PSGL-I). *Glycoconj. J.*, 15,975.
Aeed, P.A., Geng, J.G., Asa, D., Raycroft, L., Ma, L., and Elhammer, A.P. (2001) Partial characterization of the N-linked oligosaccharide structures on P-selection glycoprotein ligand-a (PSGL-1), *Cell, Res.*, 11, 28.
Alkhunaizi, AM., de Mattos, A.M., Bariy, J.M., Bennett, W.M., and Noiman, D.J. (1999) Renal transplantation across the ABO barrier using A2 kidneys. *Transplantation*, 67, 1319.
Benjamin, R.J. and Antin, J.H. (1999) ABO-incompatible bone marrow transplantation: the transfusion of incompatible plasma may exacerbate regimen-related toxicity. *Transfusion*, 39, 1273.
Benjamin, RJ., McGurk, S., Ralston, M.S., Churchill, W.H., and Antin, J.H. (1999) ABO incompatibility as an adverse risk factor for survival after allogeneic bone marrow transplantation. *Transfusion*, 39, 179.
Bensinger. WI. (1981) Plasma exchange and immunoadsorption for removal of antibodies prior to ABO incompatible bone marrow transplant. *Artif Organs*, 5,254.
Bensinger, W.I., Baker, D.A., Buckner, C.D., Clift, R.A., and Thomas, E.D. (1981) Immunoadsorption for removal of A and B blood-group antibodies. *N. Engl. J. Med.*, 304, 160.

Bensinger, WI., Baker, D.A., Buckner, C.D., Clift, R.A., and Thomas, E.D. (1981b) In vitro and in vivo removal of anti-A erythrocyte antibody by adsorption to a synthetic immunoadsorbent. *Transfusion*, 21, 335.
Bensinger, W.I., Buckner, CD., Baker, D.A., Clift, R.A., and Thomas, E.D. (1982) Removal of specific antibody in vivo by whole blood immunoadsorption: preliminary results in dogs,), *J. Clin. Apheresis.*, 1,2.
Betteridge, A. and Watkins, W,M. (1985) Variant forms of alphal, 2fucosyltransferase in human submaxillary glands from blood group ABH "secretor" and "non-secretor" individuals. *Glycoconj. J.*, 2,61.
Beyer, T.A., Sadler, J.E. and Hill, R.L. (1980) Purification to homogeneity of H blood group beta-galactoside alpha 1 leads to 2 fucosyltransferase from porcine submaxillary gland.). *J. Biol. Chem.*, 255, 5364.
Carraway, K.L. and Hull, S.R. (1991) Cell surface mucin-type glycoproteins and mucin-like domains. *Glycobiology*, 1, 131.
Clarke, J.L. and Watkins, W.M. (1999) Expression of human alpha-a-fucosyl-transferase gene homologs in monkey kidney COS cells and modification of potential fucosyltransferase acceptor substrates by an endogenous glycosidase. *Glycobiology*, 9, 191.
Clausen, H. and Hakomori, S. (1989) ABH and related histo-blood group antigens; immunochemical differences in carrier isotypes and their distribution. *Vox. Sang.*, 56, 1.
Cooper, D.K., Ye, Y., Niekrasz, M., Kehoe, M., Martin, M., Neethling, F.A., Kosanke, S., DeBault, L.E., Worsley, G., Zuhdi, N., and others. (1993) Specific intravenous carbohydrate therapy. A new concept in inhibiting antibody-mediated rejection-experience with ABO-incompatible cardiac allografting in the baboon. *Transplantation*, 56, 769.
Donald, A. S. (1981) A-active trisaccharides Isolated from A1 and A2 blood-group-specific glycoproteins. *Eur. J Biochem.*, 120, 243.
Eld , A., Zamir, G., Yaron, I., Galun, R., Safadl, R., Schaaps, 1., Berlatzky, V., Shouval, D., and iurim, 0. (1998) Liver transplantation across the ABO barrier: the role pf plasmapheresis. *Transplant Proc.*, 30, 701.
Ernst, L.K., Rajan, V.P., Larson, RD., Ruff, M.M., and Lowe, J,B. (1989) Stable expression of blood H determinants and GDP-L-fucose: betaD-galactoside 2-alpha-L-fucosyltransferase in mouse cells after transfection with human DNA. *J. Biol. Chem.*, 264, 3436.
Fargea,O., Kelil,A.N.,Samuel,D.,Saliba,F.,Anjinaden,i.L., Debat,P., Bismuth,A., Castaing, D., and Bismuth, H. (1995) The use of ABO-incompatible grafts in liver transplantation: a life-saving procedure in highly selected patients. *Transplantation*, 59, 1124.
Gale, R.P., Feig, S., Ho, Falk, P., Rippee, C., and Sparkes, R. (1977) ABO blood group system and bone marrow transplantation. *Blood*, 50, 185.

(Continued)

Primary Examiner—David A. Saunders
Assistant Examiner—F. Pierre VanderVegt
(74) Attorney, Agent, or Firm—Mintz, Levin, Cohn, Ferris, Glovsky and Popeo, P.C.; Ivor R. Elrifi; Cynthia A. Kozakiewicz

(57) ABSTRACT

The present invention provides compositions and methods for treating or preventing antibody mediated graft rejection.

8 Claims, 6 Drawing Sheets

OTHER PUBLICATIONS

Galili, U. and Matta, K.L. (1996) Inhibition of anti-Gal IgG binding to porcine endothelial cells by synthetic oligosaccharides. *Transplantation*, 62, 256.

Gibbons, RD., Meltzer, D., and Duan, N. (2000) Waiting for organ transplantation. Institute of Medicine Committee on Organ Transplantation. *Science*, 287, 237.

Gugenheim, J., Samuel, D., Reynes, M., and Bismuth, H. (1990) Liver transplantation across A130 blood group barriers. *Lancet*, 336, 519.

Hakomori, S. (1999) Antigen structure and genetic basis of histo-blood groups A, B and 0: their changes associated with human cancer. *Biochim. Biophys. Acta*, 1473, 247.

Holgersson,J,Breimer, M.E., and Samuelsson, B.E. (1992) Basic biochemistry of cell surface carbohydrates and aspects of the tissue distribution of histo-blood group ABH and related glycosphingolipids. *APM'iS Suppl.*, 27, 18.

Ishikawa, A., Itoh, M., Ushlyama, T., Suzuki, K., and Fujita, K. (1998) Experience of ABO-incompatible living kidney transplantation after double filtration plasinaphersis. *Clin. Transplant.*, 12, 80.

Kelly, Ri., Rouquier, S., Giorgi, D., Lennon, G.G., and Lowe, J.B (1995) Sequence and expression of a candidate for the human Secretor blood group alpha(1, 2)fucosyltransferase gene (FUT2). Homozygosity for an enzyme-inactivating nonsense mutation commonly correlates with the non- secretor phenotype.). *Biol. Chem.*, 270,4640.

Kumazaki, T. and Yoshida, A. (1984) Blochemical evidence that secretor gene, Se, is a structural gene encoding a specific fucosyltransferase. *Proc. NatlAcad. Sci. USA*, 81,4193.

Kyprianou, P., Betteridge, A. Donald, A.S., and Watkins, W.M. (1990) Purification of the blood group Hgeneassociatedalpha-2-L-fucosyltransferase from human plasma. *Glycoconj. J.*, 573.

Laemmli, U.K. (1970) Cleavage of structural proteins during the assembly of the head of bacteriophage 14. *Nature*, 227, 680.

Larsen, R,D., Ernst, L.K., Nair, R.P., and Lowe, J.B. (1990) Molecular cloning, sequence, and expression of a human GDP-L-fucose:beta-D-galactoside 2-alpha-L-fucosyltransferase cDNA that can form the H blood group antigen. *Proc. Nail Acad. Sci. USA*, 87,6674.

Le Pendu, I., Carton, J.P., Lemieux, R.U., and Oriol, R. (1985) The presence of at least two different H-blood-group-related beta-D-gal alpha-2-L-fuco-syltransferases in human serum and the genetics of blood group H substances. *Am. J. Hum. Genet.*, 37,749.

Liu, J. Qian, Y., and Holgersson, 1. (1997) Removal of xenoreactive human anti-pig antibodies by absorption on recombinant mucin-containing glycoproteins carrying the Gal alphal, 3Gal epitope. *Transplantation*, 63, 1673-1682.

Liu, Y., Fujitani, N., Koda, V., Soejima, M., and Klmura, H. (1999) Presence of H type 3/4 chains of ABO histo-bblood group system in serious cells of human submandibular gland and regulation of their expression by the secretor gene (FUT2) *J. Histochem. Cytochem.*, 47,889.

Liu, V. H., Fujitani, N., Koda, V., and Kimura, H. (1998) Distribution of H type I and of H type 2 antigens of ABO blood group in different cells of human submandibular gland.). *J. Histochem. Cytochem.*, 46, 69.

Lowe, I. B. (1999) Structures common to different types of glycans. In Varkl, A., Cummings, R., Esko, J., Freeze, H., Hart, G., and Marth, J.. eds., Essentials of Glycobiology. Cold Spring Harbor Laboratory Press, Cold Spring Harbor, New York, 211-252.

Porter, K.A. (1963) Morphological aspects of renal homograft rejection. *Br. Med. Bull.*, 21, 171.

Prieto, P.A., Mukerji, P., Kelder, B., Emey, R., Gonzalez, D., Yun JS., Smith, D.F., Moremen, K.W., Nardelli, C., Pierce, M., and others. (1995) Remodeling of mouse milk glycoconjugates by transgenic expression of a human glycosyltransferase. *J. Biol. Chem.*, 270, 29515.

Rajan, V.P., Larsen, RD., Ajmera, S., Ernst, L.K., and Lowe, J.B. (1989)A cloned human DNA restriction fragment determines expression of a GDP-L-fucose: beta-D-galactoside 2-alpha-L-fucosyltransferase in transfected cells. Evidence for Isolation and transfer of the human H blood group locus. *J. Biol. Chem.*, 264, 11158.

Rieben, R., Korchagina, E.Y., von Allmen, E., Hovinga, I.K., Lammle, B., iungi, T.W., Bovin, N.y., and Nydegger, U.E. (1995) In vitro evaluation of the efficacy and biocompatibility of new, synthetic ABO immunoabsorbents. *Transplantation*, 60,425.

Rouquier, S., Lowe, J.B., Kelly, RI.. Fertitta, AL., Lennon, G.G., and Glorgi. D. (1995) Molecular cloning of a human genomic region containing the H blood group alpha(1, 2)fucosyltransferase gene and two H locus-related DNA restriction fragments. Isolation of a candidate for the human Secretor blood group locus.). *J. Biol. Chem.*, 270,4632.

Sanchez-Urdazpal, L., Batts, K.P., Gores, G.I., Moore, S.B., Sterioft, S., Wiesner, R.H., and Krom, R.A. (1993) Increased bile duct complications In liver transplantation across the ABO barrier. *Ann. Surg.*, 218, 152.

Sarnesto, A., Kohlin, 1., Hindsgaul, 0., Thurin, J., and Blaszczyk-Thurin, M. (1992) Purification of the secretor-type beta-galactoside alpha 1-2-fucosyltransferase from human serum.). *J. Biol. Chem.*, 267, 2737.

Sarnesto, A. Kohlin, T., Thurin, I., and Blaszczyk-Thurin, M. (1990) Purification of H gene-encodede beta-galactoside alpha 1-2 fucosyltransferase from human serum *J. Biol. Chem.*, 265, 15067.

Seed, B. (1997) An LFA-3 cDNA encodes a phospholipid-linked membrane protein homologous to Its receptor CD2. *Nature.*, 329, 840.

Shimizu, V. and Shaw, S. (1983) Cell adhesion. Mucins in the mainstream. *Nature*, 366,630.

Silverman, H.S., Perry, S., Sutton-Smith, M., Burdick, M.D., McDermott, K., Reld, C.J., Batra, S.K., Morris, H.R., Hollingsworth, M.A., Dell, A., and Harris, A. (2001)In vivo glycosylation of mucin tandem repeais. *Glycobiology*, 11,459.

Simon,P.M.,Neethling,F.A.,Taniguchl,S.,Goode,P.L,Zopf, D.,Hancock, W.W., and Cooper, D.K. (1998) Intravenous Infusion of Galalphal-3Gal oligosaccharides in baboons delays hyperacute rejection of porcine heart xenografts. *Transplantation*, 65, 346.

Takasaki, S., Yamashita, K., and Kobata, A. (1978) The sugar chain structures of ABO blood group active glycoprotein obtained from human erythrocyte membraned. *J. Biol. Chem.*, 253,2086.

Tamaki, T., Tanaka, M., Katori, M., Osanai, M., Meguro, I., Kukita, K., Yonekawa, M., and Kawamura, A. (1998) Cryofiltration apheresis for major ABO-incompatible kidney transplantation. *Ther, Apher.*, 2, 308.

Tanabe, K., Takahashl, K., Sonda, K., Tokumoto, 1., Ishikawa, N., Kawai, T., Fuchinoue, S., Oshima, 1., Yagisawa, 1., Nakazawa, H., and others. (1998) Long-term results of ABO-incompatible living kidney transplanation: a single- center experience. *Transplantation*, 65, 224.

Wilkins, PP., McEver, R.P., and Cummings, RD. (1996) Structures of the 0-glycans on P-selectin glycoprotein ligand-l from HL-60 cells. *J. Biol. Chem.*, 271, 18732.

Yamamoto, F., Clausen, H., White, 1., Marken, J., and Hakomori, S. (1990) Molecular genetic basis of the histo-blood group ABO system. *Nature*, 345, 229.

Yeh, J.C., Hiraoka, N., Petryniak, B., Nakayama, J., Ellies, L.G., Rabuka, D., Hindsgaul, O., Marth, ID., Lowe, i.B., and Fukuda, M. (2001) Novel sulfated lymphocyte homing receptors and their control by a core 1 extension beta 1, 3-N-acetylglucosaminyltransferase. *cell*, 105, 957.

Zerfaoul, M., Fukuda, M., Sbarra, V., Lombardo, D., and El-Battari, A. (2000) Alpha(1, 2)-fucosylation prevents slalyl Lewis x expression and Eselectin-mediated adhesion of fucosyltransferase VII-transfected cells. *Eur. J. Biochem.*, 267,53.

International Search Report for PCT/IB 02/03379 mailed on Mar. 31, 2003.

Lofting, J., Hauzenberger, E., and Holgersson, J. (2002). Absorbtion of anti-blood group A antibodies on P-selectin glycoprotein ligand-1/Immunoglobulin chimeras carrying blood group A determinants: core saccharide chain specificity of the Se and H gene encoded Alpha1,2 fucosyltransferase in different host cells. *Glycobiology* 12, 173.

Prieto, P., Larsen, R., Cho, M., Rivera H., Shilatifard, A., Lowe, J., Cummings, R., and Smith, D. (1997). Expression of Human H-type Alpha1,2-Fucosyltransferase encoding for blood group H(O) antigen in chinese hamster ovary cells *J Biol Chem*, 272, 2089.

Ye, y., Niekerasz, M., Kehoe, M. Rolf, L., Martin, M., Baker, J., Kosanke, S., Romano, E., Zuhdi, N., and Cooper, D. (1994). Cardiac allostransplantation across the ABO-blood group barrier by the neutralization of performed antibodies: The baboon as a model for the human *Laboratory Animal Sci* 44, 121.

* cited by examiner

BLOOD GROUP ANTIGEN FUSION POLYPEPTIDES AND METHODS OF USE THEREOF

RELATED APPLICATIONS

This application claims priority to U.S. Ser. No. 60/306,984, filed Jul. 20, 2001, the contents of which is incorporated herein by reference in its entirety.

FIELD OF THE INVENTION

The invention relates to generally to compositions and methods for treating or preventing antibody-mediated graft rejection and more particularly to compositions including fusion polypeptides comprising blood group determinants

BACKGROUND OF THE INVENTION

The major human blood group system, the histo-blood group ABO system, is defined by three carbohydrate determinants, the blood group A, B, and H epitopes. Glycans carrying the ABH determinants are found on glycoproteins, on glycolipids, or as free oligosaccharides. ABH antigens can be found on N- or O-linked glycans. The most common core structures described so far on O-linked glycans are core 1 (Galβ3GalNAc), core 2 (Galβ3(GlcNAcβ6)GalNAc), core 3 (GlcNAcβ3GalNAc), and core 4 (GlcNAcβ3(GlcNAcβ6)GalNAc). These have been shown to carry type 1 (Galβ3GlcNAc), type 2 (Galβ4GlcNAc), and type 3 (Galβ3GalNAcα) structures Type 1 structures are mainly found as extensions of the core 3 and 4 structures, whereas type 2 chains (polylactosamine) are seen as extensions on the GlcNAcβ1,6 branch of core 2 structures.

Transplantation (Tx) across the ABO barrier is usually avoided in organ Tx because the risk of antibody-mediated rejection (AMR) due to preformed antibodies is often high This may also hold true in bone marrow transplantation, though it has long been the belief that blood group ABH incompatibility does not affect the outcome. However, in some cases it would still be desirable to transplant across the ABO barrier, one of the reasons being that it widens the pool of available donors for a particular recipient, even if it does not increase the total number of donors Removal of anti-A or anti-B antibodies by extracorporeal immunoabsorption (EIA) or plasmapheresis (PP) has been shown to improve graft survival following ABO-incompatible organ Tx. Another method used for the prevention of AMR in both ABO-incompatible Tx and xeno-Tx is infusion of free oligosaccharides, but low affinity of antibodies for free saccharides and the short half-life of low-molecular-weight oligosaccharides in the circulation (Ye et al, 1994; Simon et al., 1998) prevents a wider use.

SUMMARY OF THE INVENTION

The invention is based in part on the discovery that blood group epitopes can be specifically expressed at high density and by different core saccharides chains on mucin-type protein backbones. The polypeptides, are referred to herein as ABO fusion polypeptides.

In one aspect, the invention provides a fusion polypeptide that includes a first polypeptide, comprising at least a region of a mucin polypeptide, glycosylated by a α1,2 fucosyltransferase operably linked to a second polypeptide. The first polypeptide is sequentially glycosylated by an α1,3 N-acetylgalactosaminyl transferase and/or a α1,3 galacto-syltransferase. The mucin polypeptide is for example PSGL-1. Preferably, the mucin polypeptide is the extracellular portion of PSGL-1. The α1,2 fucosyltransferase is for example a blood group H or Secretor α1,2, fucosyltransferase such as FUT1 or FUT2.

In preferred embodiments, the second polypeptide comprises at least a region of an immunoglobulin polypeptide. For example, the second polypeptide comprises a region of a heavy chain immunoglobulin polypeptide. Alternatively, the second polypeptide comprises the FC region of an immunoglobulin heavy chain.

The ABO fusion polypeptide is a mutimer. Preferably, the ABO fusion polypeptide is a dimer.

Also included in the invention is a nucleic acid encoding an ABO fusion polypeptide, as well as a vector containing ABO fusion polypeptide-encoding nucleic acids described herein, and a cell containing the vectors or nucleic acids described herein. Alternatively the vector further comprises a nucleic acid encoding a α1,2, fucosyltransferase and/or a α1,3 N acetylgalactosaminyltransferase or a α1,3 galacto-syltransferase In another aspect, the invention provides a method of treating antibody-mediated rejection in a subject. The method includes contacting a biological sample, e.g., whole blood or plasma from a subject with the ABO fusion polypeptide of the invention to form an fusion polypeptide-antibody complex. The complex is removed from the biological sample and the biological sample is refused into the subject.

Also included in the invention is a method of removing an antibody from a sample by contacting the sample with the ABO fusion peptide of the invention to form an antibody-fusion peptide complex and removing the complex from the biological sample.

Also included in the invention are pharmaceutical compositions that include the ABO fusion polypeptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
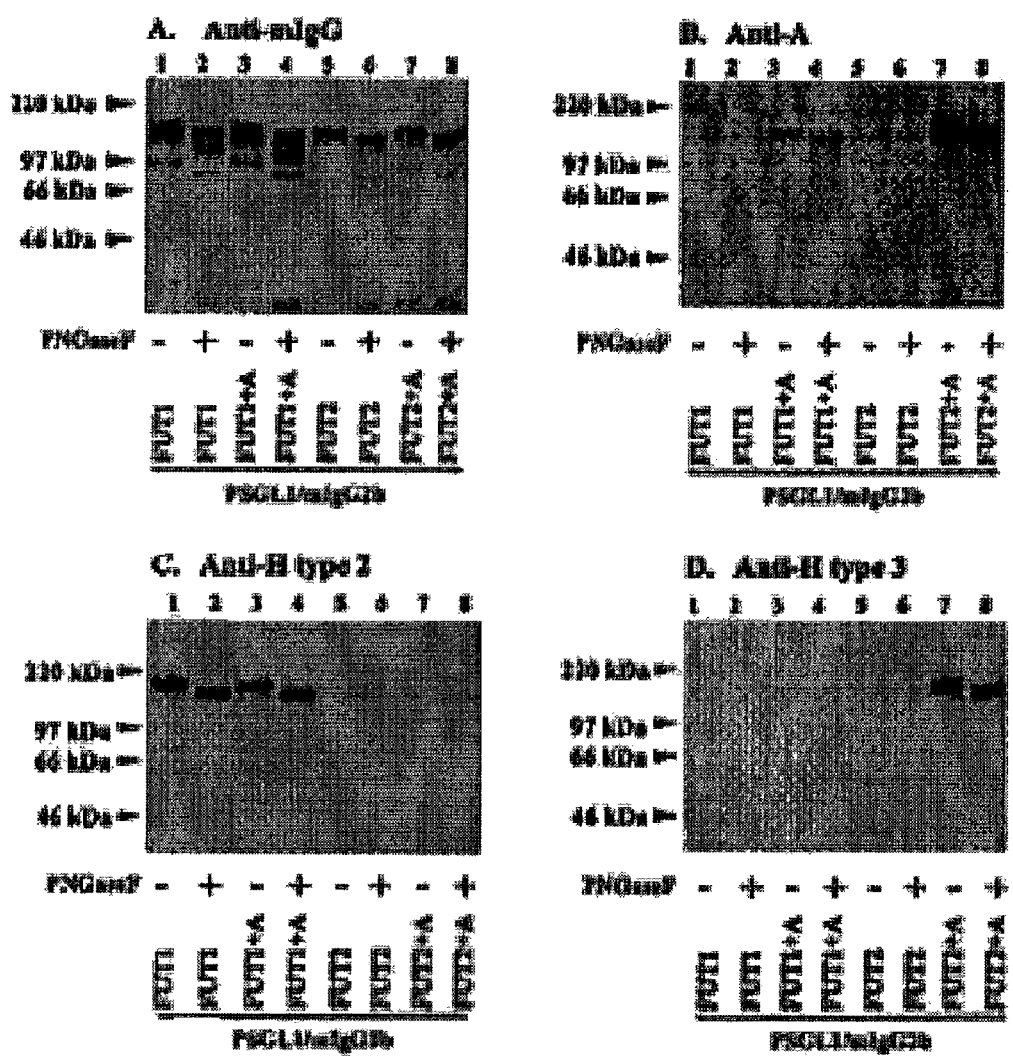
FIGS. 1A-D are photographs of SDS-PAGE and western blot analysis of immunopurified PSGL-1/m 1 gG$_{2b}$, chimeras produced in 293T cells transfected with the H or Se gene alone, or in combination with the A gene encoded α1,3 GalNAcT. Following separation on an 8% SDS-PAGE and blotting onto nitrocellulose membranes, the PSGL-1/mIgG$_{2b}$, chimeras were probed with an anti-mouse IgG antibody (A), an anti-blood group A antibody followed by a goat anti-mouse IgM antibody (B), an anti-H type 1 chain-specific antibody followed by a HRP-labelled goat anti-mouse IgG$_3$ antibody (C), an anti-H type 2 chain-specific antibody followed by a goat anti-mouse IgM-HRP antibody (D), and an anti-H type 3 chain-specific antibody followed by a HRP-labeled goat anti-mouse IgM antibody (E). In panels A-D, samples analyzed were from cells transfected with plasmids encoding CDM8 (lanes 1 and 5), PSGL-1/mIgG$_{2b}$, (lanes 2 and 6), PSGL-1/mIgG$_{2b}$ and the H gene (lane 3), PSGL-1/mIgG$_{2b}$, the H and A gene (lane 4), PSGL-1/mIgG$_{2b}$, and the Se gene (lane 7), or PSGL-1/mIgG$_{2b}$, and the Se and A gene (lane 8). In E the duplicate samples from CDM8 and PSGL-1/mIgG$_{2b}$ transfected cells were omitted. In C, 250 ng of H-type 1 chain-BSA was used as a positive control.

The invention is based in part in the discovery that blood group epitopes can be specifically expressed at high density and by different core saccharides chains on mucin-type protein backbones. This higher density of blood group eptiopes results in an increased binding or removal (i.e., absorption) of anti-blood group antibodies as compared to free saccharides, or AB determinants linked to solid phase.

The invention provides mucin-immunoglobulin fusion proteins (refered to herein as "ABO fusion proteins") containing multiple blood group epitopes that are useful as an absorber for anti-blood group antibodies. The ABO fusion peptides are also useful as a model protein for studies on glycosylation. For example, the ABO fusion protein are useful in eliminating recipient anti-blood group ABO antibodies from blood or plasma prior to an ABO incompatible organ or bone marrow transplantation. The ABO fusion protein absorbs 50%, 60%, 70%, 80%, 90%, 95%, 98% or 100% of anti-blood group ABO antibodies from recipient blood or plasma.

The ABO fusion peptide is more efficient on a carbohydrate molar basis in removing or binding anti-blood group antibodies as compared free saccharides of wild type AB determinants. The ABO fusion peptide binds 2, 4, 10, 20, 50, 80, 100 or more-fold greater number of anti-blood group antibodies as compared to an equivalent amount of free saccharides of wild type AB determinants.

The ABO fusion proteins of the invention carries an epitope specific for a blood group determinants. For example, the ABO fusion protein carries either the A epitope, the B epitope or the H epitope. Alternatively, the ABO fusion carries two epitope for blood group antigens. For example the ABO fusion protein carries both the A and B epitope. In some aspects the ABO fusion protein carries all three epitopes (i.e., A, B and H).

Fusion Polypeptides

In various aspects the invention provides fusion proteins that include a first polypeptide containing at least a portion of a glycoprotein, e.g., a mucin polypeptide operatively linked to a second polypeptide. As used herein, a "fusion protein" or "chimeric protein" includes at least a portion of a mucin polypeptide operatively linked to a non-mucin polypeptide. A "mucin polypeptide" refers to a polypeptide having a mucin domain. The mucin polypeptide has one, two, three, five, ten, twenty or more mucin domains. The mucin polypeptide is any glycoprotein characterized by a amino acid sequence subsitited with O-glycans. For example a mucin polypeptide has every second or third amino acid being a serine or threonine. The mucin polypeptide is a secreted protein. Alternatively, the mucin polypeptide is a cell surface protein.

Mucin domains are rich in the amino acids threonine, serine and proline, where the oligosaccharides are linked via N-acetylgalactosamine to the hydroxy amino acids (O-glycans). A mucin domain comprises or alternatively consists of an O-linked glycosylation site. A mucin domain has 1, ,2, 3, 5, 10, 20, 50, 100 or more O-linked glycosylation sites. Alternatively, the mucin domain comprises or alternatively consists of a N-linked glycosylation site. A mucin polypeptide has 50%, 60%, 80%, 90%, 95% or 100% of its mass due to the glycan. A mucin polypeptide is any polypeptide encode for by a MUC genes (i.e., MUC1, MUC2, MUC3, etc.) Alternatively, a mucin polypeptide is P-selectin glycoprotein ligand 1 (PSGL-1), CD34, CD43, CD45, CD96, GlyCAM-1, MAdCAM or red blood cell glycophorins. Preferably, the mucin is PSGL-1. Whereas a "non-mucin polypeptide" refers to a polypeptide of which at least less than 40% of its mass is due to glycans.

Within an ABO fusion protein of the invention the mucin polypeptide can correspond to all or a portion of a mucin protein. In one embodiment, an ABO fusion protein comprises at least a portion of a mucin protein. "At least a portion" is meant that the mucin polypeptide contains at least one mucin domain (e.g., an O-linked glycosylation site). In one embodiment, the mucin protein comprises the extracellular portion of the polypeptide. For example, the mucin polypeptide comprises the extracellular portion of PSGL-1.

The first polypeptide is glycosylated by one or more blood group transferases. The first polypeptide is glycosylated by 2, 3, 5 or more blood group transferases. Glycosylation is sequential or consecutive. Alternatively glycosylation is concurrent or random, i.e., in no particular order. For example the first polypeptide is glycosylated by an α1,2 fucosyltransferase, such as the H- or Se-gene encoded α1,2 fucosyltransferases. Exemplary α1,2 fucosyltransferases are FUT1 (Gen Bank AcC. Nos: Q10984; O10983; O10981; AT455028 and NM00148)and FUT2. (Gen Bank AcC. No: P19526; BAA11638; D82933 and A56098) Alternatively, the first polypeptide is glycosylated by 1,3 N-acetylgalactosaminyltransferase or α1,3 galactosaminyltransferase. In some aspects, the first polypeptide is glycosylated by both an α1,2 fucosyltransferase and a 1,3 N-acetylgalactosaminyltransferase or a α1,3 galactosaminyltransferase.

Within the fusion protein, the term "operatively linked" is intended to indicate that the first and second polypeptides are chemically linked (most typically via a covalent bond such as a peptide bond) in a manner that allows for O-linked glycosylation of the first polypeptide. When used to refer to nucleic acids encoding a fusion polypeptide, the term operatively linked means that a nucleic acid encoding the mucin polypeptide and the non-mucin polypeptide are fused in-frame to each other. The non-mucin polypeptide can be fused to the N-terminus or C-terminus of the mucin polypeptide.

In a further embodiment, the ABO fusion protein may be linked to one or more additional moieties. For example, the ABO fusion protein may additionally be linked to a GST fusion protein in which the ABO fusion protein sequences are fused to the C-terminus of the GST (i.e., glutathione S-transferase) sequences. Such fusion proteins can facilitate the purification of ABO fusion protein. Alternatively, the ABO fusion protein may additionally be linked to a solid support. Various solid support are know to those skilled in the art. Such compositions can facilitate removal of anti-blood group antibodies. For example, the ABO fusion protein is linked to a particle made of, e.g., metal compounds, silica, latex, polymeric material; a microtiter plate; nitrocellulose, or nylon or a combination thereof. The ABO fusion proteins linked to a solid support are used as an absorber to remove anti-blood group antibodies from a biological sample, such as blood or plasma.

In another embodiment, the fusion protein is includes a heterologous signal sequence (i.e., a polypeptide sequence that is not present in a polypeptide encoded by a mucin nucleic acid) at its N-terminus. For example, the native mucin signal sequence can be removed and replaced with a signal sequence from another protein. In certain host cells (e.g., mammalian host cells), expression and/or secretion of polypeptide can be increased through use of a heterologous signal sequence.

An chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

ABO fusion polypeptides may exist as oligomers, such as dimers, trimers or pentamers. Preferably, the ABO fusion polypeptide is a dimer.

The first polypeptide, and/or nucleic acids encoding the first polypeptide, can be constructed using mucin encoding sequences are known in the art. Suitable sources for mucin polypeptides and nucleic acids encoding mucin polypeptides include GenBank Accession Nos. NP663625 and NM145650, CAD10625 and AJ417815, XP140694 and XM140694, XP006867 and XM006867 and NP00331777 and NM009151 respectively, and are incorporated herein by reference in their entirety.

In some embodiments, the mucin polypeptide moiety is provided as a variant mucin polypeptide having a mutation in the naturally-occurring mucin sequence (wild type) that results in increased carbohydrate content (relative to the non-mutated sequence). For example, the variant mucin polypeptide comprised additional O-linked glycosylation sites compared to the wildtype mucin. Alternatively, the variant mucin polypeptide comprises an amino acid sequence mutations that results in an increased number of serine, threonine or proline residues as compared to a wild type mucin polypeptide. This increased carbohydrate content can be assessed by determining the protein to carbohydrate ratio of the mucin by methods know to those skilled in the art.

In some embodiments, the mucin polypeptide moiety is provided as a variant mucin polypeptide having mutations in the naturally-occurring mucin sequence (wild type) that results in a mucin sequence more resistant to proteolysis (relative to the non-mutated sequence).

In some embodiments, the first polypeptide includes full-length PSGL-1. Alternatively, the first polypeptide comprise less than full-length PSGL-1 polypeptide such as the extracellular portion of PSGL-1. For example the first polypeptide less than 400 amino acids in length, e.g., less than or equal to 300, 250, 150, 100, 50, or 25 amino acids in length. Exemplary PSGL-1 polypeptide and nucleic acid sequences include GenBank Access No: XP006867; XM006867; XP140694 and XM140694.

The second polypeptide is preferably soluble. In some embodiments, the second polypeptide includes a sequence that facilitates association of the ABO fusion polypeptide with a second mucin polypeptide. In preferred embodiments, the second polypeptide includes at least a region of an immunoglobulin polypeptide. "At least a region" is meant to include any portion of an immunoglobulin molecule, such as the light chain, heavy chain, FC region, Fab region, Fv region or any fragment thereof. Immunoglobulin fusion polypeptide are known in the art and are described in e.g., U.S. Pat. Nos. 5,516,964; 5,225,538; 5,428,130;5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light chain, Fab, $Fab_2$, Fv, or Fc. Preferably, the second polypeptide includes the heavy chain of an immunoglobulin polypeptide. More preferably the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

Another aspect of the invention pertains to vectors, preferably expression vectors, containing a nucleic acid encoding mucin polypeptides, or derivatives, fragments, analogs or homologs thereof. In various aspects the vector contains a nucleic acid encoding a mucin polypeptide operably linked to an nucleic acid encoding an immunoglobulin polypeptide, or derivatives, fragments analogs or homologs thereof. Additionally, the vector comprises a nucleic acid encoding a blood group transferase such as a $\alpha$1,2 fucosyltransferase, a $\alpha$1,3 N acetylgalactosamininytransferase, a $\alpha$1,3 galactosyltransferase or any combination thereof. The blood group transferase facilitates the addition of blood group determinants on the peptode backbone of the mucin portion of the ABO fusion protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ABO fusion polypeptides, mutant forms of ABO fusion polypeptides, etc.).

The recombinant expression vectors of the invention can be designed for expression of ABO fusion polypeptides in prokaryotic or eukaryotic cells. For example, ABO fusion polypeptides can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the ABO fusion polypeptide expression vector is a yeast expression vector. Examples of vectors for expression in yeast *Saccharomyces cerivisae* include pYepSec1 (Baldari, et al., 1987. *EMBO J* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, ABO fusion polypeptide can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention is expressed in mammalian cells using a mammalian expression vector. Examples of mammalian expression vectors include pCDM8 (Seed, 1987. *Nature* 329: 846) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, glycoprotein Ibα fusion polypeptides can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding glycoprotein Ibα fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) ABO fusion polypeptides. Accordingly, the invention further provides methods for producing ABO fusion polypeptides using the host cells of the invention. In one embodiment, the method comprises culturing the host cell of invention (into which a recombinant expression vector encoding ABO fusion polypeptides has been introduced) in a suitable medium such that ABO fusion polypeptides is produced. In another embodiment, the method further comprises isolating ABO polypeptide from the medium or the host cell.

The ABO fusion polypeptides may be isolated and purified in accordance with conventional conditions, such as extraction, precipitation, chromatography, affinity chromatography, electrophoresis or the like. For example, the immunoglobulin fusion proteins may be purified by passing a solution through a column which contains immobilized protein A or protein G which selectively binds the Fc portion of the fusion protein. See, for example, Reis, K. J., et al., J. Immunol. 132:3098-3102 (1984); PCT Application, Publication No. WO87/00329. The fusion polypeptide may the be eluted by treatment with a chaotropic salt or by elution with aqueous acetic acid (1 M).

Alternatively, an ABO fusion polypeptides according to the invention can be chemically synthesized using methods known in the art. Chemical synthesis of polypeptides is described in, e.g., A variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241-247 (1986); Barany, et al, *Intl. J. Peptide Protein Res.* 30: 705-739 (1987); Kent, *Ann. Rev. Biochem.* 57:957-989 (1988), and Kaiser, et al, *Science* 243: 187-198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J Med. Chem.* 36: 2585-2594; Kirby, et al., 1993. *J. Med. Chem.* 36:3802-3808; Morita, et al., 1994. *FEBS Lett.* 353: 84-88; Wang, et al., 1993. *Int. J. Pept. Protein Res.* 42: 392-399; Fauchere and Thiunieau, 1992. *Adv. Drug Res.* 23: 127-159.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182-5185 (1996)), or between two amino acid side chains. See, e.g., DeGrado, *Adv Protein Chem*, 39: 51-124 (1988). Disulfide bridges are also introduced into linear sequences to reduce their flexibility. See, e.g., Rose, et al., *Adv Protein Chem*, 37: 1-109 (1985); Mosberg et al., *Biochem Biophys Res Commun*, 106: 505-512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications*, Gutte, ed., Academic Press pp. 287-320 (1995).

Methods of Treating or Preventing Antibody-Mediated Graft Rejection

Also included in the invention are methods of treating or preventing antibody mediated graft rejection (AMR), e.g., organ transplant rejection. Such transplants include but are not limited to kidney, liver, skin, pancreas, cornea, or heart. AMR is meant to include any antibody mediated graft rejection by the recipient. The method includes contacting a biological sample from a subject with the ABO fusion peptide of the invention. The biological sample is for example, blood, i.e., whole blood or plasma. The sample is know to or suspected of comprising an antibody, e.g., an anti-blood group antibody. In some aspects, the biological sample is withdrawn from the subject prior to contacting the sample with the ABO fusion polypeptide. The biological sample is contacted with the ABO fusion peptide under conditions to allow formation of an ABO fusion peptide-anti-blood group antibody complex. The ABO fusion peptide-complex, if present is separated from the biological sample to eliminate the anti-blood group antibodies and the biological sample is reinfused into the subject. AMR is also treated or prevented by administering to a subject an ABO fusion polypeptide of the invention.

The subject can be e.g., any mammal, e.g., a human, a primate, mouse, rat, dog, cat, cow, horse, pig. The treatment is administered prior to the subject receiving an ABO-incompatible transplant. Alternatively, treatment is administered after a subject receives an ABO incompatible transplant.

The biological sample is contacted with the ABO fusion protein by methods know to those skilled in the art. For example, plasmapheresis or extracorporeal immunoabsorption.

Essentially, any disorder, which is etiologically linked to an antibody mediated reaction is considered amenable to prevention or to treatment. AMR is treated or prevent when the survival rate of the organ transplant is greater than an organ transplant not treated by the method of the invention. By survival rate of the transplant is meant the time before the transplant is rejected by the recipient For example, AMR is treated or prevent when the transplant survives at least 1, 2, 4 or 8 weeks after transplant. Preferably, the transplant survives 3, 6, 13 months. More preferably, the transplant survives 2, 3, 5 or more years.

Methods of Removing Anti-blood Group Antibodies from a Sample

Also included in the invention are methods of removing or depleting anti-blood group antibodies from a sample. The sample is a biological fluid such as blood or plasma. Alternatively, the sample is a biological tissue, such as heart tissue, liver tissue, skin, or kidney tissue. The method includes contacting a sample with the ABO fusion peptide of the invention. The sample is contacted with the ABO fusion peptide under conditions to allow formation of an ABO fusion peptide-anti-blood group antibody complex. The ABO fusion peptide-antibody complex, if present is separated from the biological sample to remove or deplete the anti-blood group antibodies.

Pharmaceutical Compositions Including ABO Fusion Polypeptides or Nucleic Acids Encoding Same The ABO fusion proteins, or nucleic acid molecules encoding these fusion proteins, (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ABO fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

The invention will be further illustrated in the following non-limiting examples.

EXAMPLE 1

General Methods

The data described herein was generated using the following reagents and methods.

Cell Culture

COS-7 m6 cells (Seed, 1987), CHO-K1 (ATCC CCL-61), and the SV40 Large T antigen expressing 293 human embryonic kidney cell line (293T; kindly provided by B. Seed), were cultured in Dulbecco's modified Eagle's medium (GibcoBrl, Life Technologies, Paisley, Scotland), supplemented with 10% fetal bovine serum (GibcoBrl, Life Technologies), 25 µg/ml gentamycin sulfate (Sigma, St. Louis, Mo.) and 2 mM glutamine (GibcoBrl, Life Technologies). The cells were passaged every 2-4 days. The HH14 hybridoma (ATCC HB-9299; U.S. Pat. No. 4,857,639) were cultured in RPMI 1640 (GibcoBrl, Life Technologies), supplemented with 10% fetal bovine serum, 100 U/ml of penicillin, 100 µg/l of streptomycin, and 2 mM glutamine.

Purification of HH14 Antibodies

Supernatant was collected from cultured HH14 cells. Two liters of supernatant was affinity purified on a goat anti-mouse IgM (Sigma) column, using a Bio-Rad LP chromatograph (Bio-Rad, Hercules, Calif.). The bound proteins were eluted by 0.1 M glycine-Cl, pH 2.5, and the eluate was immediately neutralized using 1 M Tris-Cl, pH 7.5. The eluate was dialyzed against 1% phosphate-buffered saline (PBS) and lyophilized. Lyophilized proteins were dissolved in distilled $H_2O$ to a final concentration of 3 µg/µl, as measured by the BCA assay.

Construction of Expression Vectors

The human blood group A gene was polymerase chain reaction (PCR) amplified off cDNA made from total RNA isolated from the MKN-45 cell line, using 5'-cgc ggg aag ctt gcc gag acc aga cgc gga-3' (SEQ ID NO:1) as forward primer and 5'-cgc ggg cgg ccg ctc acg ggt tcc gga ccg c-3' (SEQ ID NO:2) as reverse primer. The amplified cDNA (A gene) was subcloned into the polylinker of CDM8 (Seed, 1987) using Hind III and Not I. The blood group H gene was PCR amplified in two pieces using a human tonsil stroma library as the template. An internal Sse I site was created by PCR using internal overlapping primers changing nucleotide 775 (GenBank accession no. M35531) to a C, creating a Sse I site of the Pst I site. The cDNA encoding the carboxy terminal of FUT1 was amplified using 5'-ggg gac tac ctg cag gtt atg cct cag cgc-3' (SEQ ID NO:3) as forward primer and 5'-cgc ggg gcg gcc gct tca agg ctt agc caa tgt-3' (SEQ ID NO:4) as reverse primer, cleaved by Sse I and Not I, and subcloned into the CDM8 expression vector digested with Pst I and Not I. The cDNA encoding the amino terminal of FUT1 was amplified using 5'-cgc ggg aag ctt acc atg tgg ctc cgg agc cat-3' (SEQ ID NO:5) as forward primer and 5'-cca gcg ctg agg cat aac ctg cag gta gtc-3' (SEQ ID NO:6) as reverse primer, cleaved by Hind III and Sse 1, and subcloned into CDM8 carrying the carboxy terminal following Hind III and Sse I cleavage.

The Se gene was similarly PCR amplified from cDNA reversely transcribed from total RNA isolated from peripheral blood mononuclear cells donated by a blood group $A_2Le(a-b+)Se$ individual, using 5'-cgc ggg aag ctt acc atg ctg gtc gtt cag atg-3' (SEQ ID NO:7) as forward primer and 5'-cgc ggg cgg ccg ctt agt gct tga gta agg g-3' (SEQ ID NO:8) as reverse primer. The Se gene cDNA was subcloned into CDM8 using Hind III and Not I. Glycosyltransferase cDNAs were sequenced and the enzymatic activity they encoded checked by flow cytometric analysis of transiently transfected cells using blood group H and A-specific monoclonal antibodies. The PSGL-1/mIgG$_{2b}$ chimera was constructed as described before (Liu et al., 1997).

Transfections and Production of Secreted PSGL-1/mIgG$_{2b}$ Chimeras

The transfection cocktail was prepared by mixing 39 μl of 20% glucose, 39 μg of plasmid DNA, 127 μl dH$_2$O, and 15.2 μl 0.1M polyethylenimine (25 kDa; Aldrich, Milwaukee, Wis.) in 5-ml polystyrene tubes. In all transfection mixtures, 13 μg of the PSGL-1/mIgG$_{2b}$ plasmid was used. Thirteen micrograms of the plasmid for the different glycosyitransferases were added, and, when necessary, the CDM8 plasmid was added to reach a total of 39 μg of plasmid DNA. The mixtures were left in room temperature for 10 min before being added in 10 ml of culture medium to the cells, at approximately 70% confluency. After 7 days, cell supernatants were collected, debris spun down (1400×g, 15 mm) and NaN$_3$ was added to a final concentration of 0.02% (w/v).

Purification of Secreted PSGL-1/mIgG$_{2b}$, for SDS-PAGE and western Blot Analysis PSGL-1/mIgG$_{2b}$ fusion proteins were purified from collected supernatants on 50 μl goat anti-mIgG agarose beads (100:1 slurry; Sigma) by rolling head over tail overnight at 4° C. The beads with fusion proteins were washed three times in PBS and used for subsequent analysis. Typically, the sample was dissolved in 50 μl of 2×reducing sample buffer and 10:1 of sample was loaded in each well.

PNGaseF Treatment of Affinity-Purified PSGL-1/mIgG$_{2b}$

A PNGaseF kit (Roche Diagnostics, Indianapolis, Ind.) was used for N-glycan deglycosylation, A slight modification of the protocol provided by the manufacturer was used. In 1.5-ml Eppendorf tubes, 20 μl of reaction buffer was mixed with purified PSGL-1/mIgG$_{2b}$ on agarose beads and boiled for 3 min. The mixture was spun down, and 10 μl of the supernatant was transferred to a new Eppendorf tube. Ten microliters of PNGaseF or, as a negative control, 10 μl of reaction buffer were added. The tubes were incubated for 1.5 h at 37° C. After incubation, 20 μl of 2×reducing sample buffer and 10 μl of H$_2$O was added, and the samples were boiled for 3 min.

ELISA for Determination of PSGL-1/mJgG$_{2b}$ Concentration in Supernatants

Ninety-six-well ELISA plates (Costar 3590, Corning, N.Y.) were coated with 0.5 μg/well of affinity-purified goat anti-mIgG specific antibodies (Sigma) in 50 μl of 50 mM carbonate buffer, pH 9.6, for two h in room temperature. After blocking o/n at 4° C. with 300 μl 3% bovine serum albumin (BSA) in PBS with 0.05% Tween (PBS-T) and subsequent washing, 50 μl sample supernatant was added, serially diluted in culture medium. Following washing, the plates were incubated for 2 h with 50 μl of goat anti-mIgM-HRP (Sigma), diluted 1:10,000 in blocking buffer. For the development solution, one tablet of 3,3',5,5'-tetramethylbenzidine (Sigma) was dissolved in 11 ml of 0.05 M citrate/phosphate buffer with 3 μl 30% (w/v) H$_2$O$_2$. One hundred microliters of development solution was added. The reaction was stopped with 25 μl 2 M H$_2$SO$_4$. The plates were read at 450 and 540 nm in an automated microplate reader (Bio-Tek Instruments, Winooski, Vt.). As a standard, a dilution series of purified mIgG Fc fragments (Sigma) in culture medium was used in triplicate.

SDS-PAGE and Western Blotting

SDS-PAGE was run by the method of Laemmli (1970) with a 5% stacking gel and an 8% resolving gel, and separated proteins were electrophoretically blotted onto Hybond™-C extra membranes as described before (Liu et al., 1997). Following blocking overnight in Tris-buffered saline with 0.05% Tween-20 (TBS-T) with 3% BSA, the membranes were washed three times with TBS-T. They were then incubated for 1 h in room temperature with mouse anti-human blood group A all types (mIgM, Dako, Carpinteria, Calif.) or anti-human H type 1 (mIgG$_3$, Signet; Dedham, Mass.), H type 2 (mIgM, Dako) or H type 3 (mIgM, hybridoma HH14, ATCC HB9299). All antibodies were diluted 1:200 in 3% BSA in TBS-T, except for the H type 3 antibody, which was diluted to a concentration of 1 μg/ml in 3% BSA in TBS-T. The membranes were washed three times with TBS-T before incubation for 1 h at room temperature with secondary horseradish peroxidase (HRP)-conjugated antibodies, goat anti-mIgM (Cappel, Durham, N.C.) or goat anti-mIgG$_3$ (Serotec, Oxford, England) diluted 1:2000 in 3% BSA in TBS-T. Bound secondary antibodies were visualized by chemiluminescence using the ECL kit (Amersham Pharmacia Biotech, Uppsala, Sweden) according to the instructions of the manufacturer. For detection of the PSGL-1/mIgG$_{2b}$ itself, HRP-labeled goat anti-mIgG (Sigma) was used at a dilution of 1:10,000 in 3% BSA in TBS-T as described, but without incubation with a secondary antibody.

Determination of the Relative Blood Group A Epitope Density on PSGL-1/mIgG$_{2b}$ Western blots were run as described above. The membranes were visualized in a Fluor-S Max Muitlmager carrying a CCD camera operating at −35° C. (BioRad). Using the volume tool in the analysis window of the Quantity One software (BioRad), the volume (sum of the intensities of the pixels within the volume boundary×pixel area) for the blood group A reactivity was divided by the volume for the mIgG reactivity for the PSGL-1/mIgG$_{2b}$ made in COS, CHO, and 293T cells. To compare the A epitope/mouse IgG ratios between PSGL-1/mIgG$_{2b}$ made in the different host cells, the ratios were normalized to the ratio obtained from the A substituted PSGL-1/mIgG$_{2b}$ made in COS cells transfected with the H and A genes.

Absorption of Serum

Six hundred microliters slurry of goat anti-mIgG agarose beads (Sigma) was transferred into 1.5-ml Eppendorf microcentrifuge tubes. The beads were spun down by a quick spin at 400 ×g. The supernatant was then removed, and the beads were washed once with 1 ml PBS, spun down again, and transferred to 180 ml of supernatant from CHO cells transfected with cDNAs encoding PSGL-1/mIgG$_{2b}$ the Se and the A gene. Supernatants containing agarose beads were incubated head over tail o/n at 4° C. For collection, the beads were spun down at 400×g, 15 min, at room temperature, and transferred to 1.5-ml Eppendorf microcentrifuge tubes. Washing was done three times with PBS. These beads are referred to as A mucin-beads. Six hundred microliters of anti-mIgG agarose beads were also prepared in the same manner, but they were used for dilution of the A mucin-beads to obtain a dilution series of the A mucin-beads as absorbents. These beads are referred to as goat anti-mIgG beads. The beads were aliquoted into 4-ml Ellerman tubes according to Table I. A-PAA-MPG (Syntesome, Munich, Germany) and B-PAA-MPG (Syntesome) were weighed and aliquoted into Ellerman tubes according to Table I, and thereafter washed once with PBS.

Pooled serum from five patients typed blood group O was obtained from the Blood Bank at Huddinge University Hospital (Ethical permission, Dnr. 392/99, approval date Aug. 15, 2000). Cell debris was removed from the serum by centrifugation at 14,000 rpm for 5 min in a Jouan A-14 microcentrifuge. The cleared serum was transferred to another tube and incubated in a waterbath at 56° C. for 1 h to inactivate complement. The serum was stored in aliquots at −20° C. until being used.

TABLE I

Serial dilutions of absorbents used for absorption of anti-blood group A antibodies from pooled serum of blood group O individuals

| Sample | Amount of absorbent |
|---|---|
| 1 | 100 µl of A mucin-beads |
| 2 | 80 µl of A mucin-beads, 20 µl of goat anti-mIgG beads |
| 3 | 60 µl of A mucin-beads, 40 µl of goat anti-mIgG beads |
| 4 | 40 µl of A mucin-beads, 60 µl of goat anti-mIgG beads |
| 5 | 20 µl of A mucin-beads, 80 µl of goat anti-mIgG beads |
| 6 | 100 µl of goat anti-mIgG beads |
| 7 | 150 mg of A~PAA~MPG[a] |
| 8 | 120 mg of A-PAA-MPG, 30 mg of B.PAA.MPG[b] |
| 9 | 90 mg of A-PAA-MPG, 60 mg of B-PAA-MPG |
| 10 | 60 mg of A-PAA-MPG, 90 mg of B-PAA-MPG |
| 11 | 30 mg of A-PAA-MPG, 120 mg of B-PAA-MPG |
| 12 | 150 mg of B-PAA-MPG |
| 13 | Only serum |

[a]A-PAA-MPG, A trisaccharides linked via poly[N-(2-hydmxyethyl)acrylamide] to macroporous glass beads.
[b]B-PAA-MPG B trisaccharides linked via poly[N-(2-hydroxymethyl)acrylamide] to macroporous glass beads.

Five hundred microliters of serum were added to each tube and mixed with the beads for 4 h on a rolling table at 4° C. Following absorption, the beads were spun down and the absorbed serum transferred to new Ellerman tubes. The absorbed serum was stored at −20° C. until further analysis.

To determine the amount of PSGL-1/mIgG$_{2b}$ on the A mucin-beads, a goat anti-mIgG Fc ELISA (see previous procedure) was run on the supernatant before and after incubation with agarose beads.

ELISA for Quantification of Anti-A Antibodies

Ninety-six-well ELISA plates (Costar 3590, Corning) were coated for 2 h at room temperature with 0.05 µl of A-PAA-biotin (Syntesome) in 50 µl per well of 50 mM carbonate buffer, pH 9.6. Following blocking o/n at 4° C. with 300 µl 3% BSA in PBS-T and subsequent washing, 50 µl of serum serially diluted in PBS were added and the plate was incubated at room temperature for 2 h. After washing, the incubation was done with 50 µl of mouse-anti-human IgA, G and M-HRP (Jackson, Pa.) diluted 1:10,000 in blocking buffer. Development and reading of the plates was done as described previously.

Determination of Total Protein Concentration in Serum

The total protein concentration in serum was determined before and after absorption of anti-A antibodies. The microtiter plate protocol of the BCA protein Assay Reagent (Pierce, Rockford, Ill.) was used according to the manufacturer's instructions, and samples were run in duplicates or triplicates.

EXAMPLE 2

Blood Group H and A Determinants on Recombinant PSGL-1/mIgG20 Made in Various Host Cells 293Tcells. Immunoaffinity-purified PSGL-1/mIgG$_{2b}$, produced by 293T cells transiently transfected with the PSGL-1/mIgG$_{2b}$ cDNA with and without the plasmids encoding the H, Se, or A genes was analyzed by sodium dodecyl sulfate-polyacrylamide gel elecrophoresis (SDS-PAGE) and western blot using anti-mIgG, anti-blood group A, H type 1, H type 2, and H type 3 specific antibodies for detection (FIGS. 1A-E). The fusion protein migrated under reducing conditions as a doublet with an apparent molecular weight of approximately 100 and 140 to 160 kDa (A). The PSGL-1/mIgG$_{2b}$ stained poorly with silver (not shown) in concordance with previous observations with respect to the behavior of highly glycosylated, mucin-type proteins (Carraway and Hull, 1991; Shimizu and Shaw, 1993). As shown before (Liu et al., 1997), the fusion protein was produced as a homodimer (data not shown). Double bands around 65 kDa and 35 kDa were detected with the anti-mIgG antibody. These bands were not seen in the supernatants of 293T cells transfected with empty vector alone and are thus likely to be proteolytic fragments derived from the fusion protein (Carraway and Hull, 1991). The 47-kDa and 20-kDa bands seen in cell fractions are derived from the heavy and light Ig chains of the goat anti-mouse antibody, which is coming off the agarose beads on boiling in sample buffer.

Figure 2:
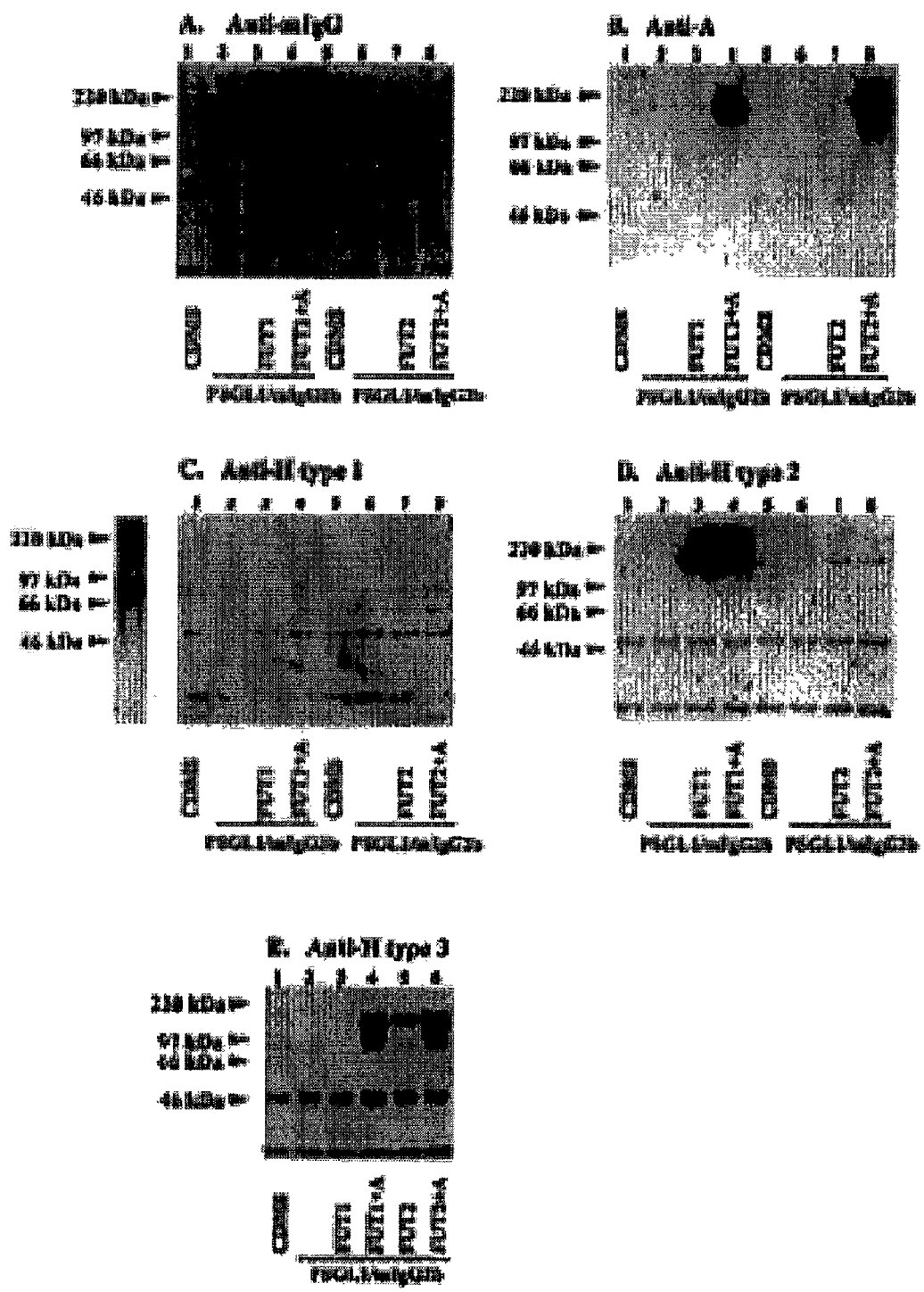
FIGS. 2 A-D are photographs of SDS-PAGE and western blot analysis of PNGaseF-treated immunopurified PSGL-1/mIgG$_{2b}$ produced in 293T cells transfected with the H or Se gene alone or in combination with the A gene encoded α1,3 GalNAcT. Following PNGaseF treatment (+), or not (−), of immunopurified PSGL-1/mIgG$_{2b}$, the PSGL-1/mIgG$_{2b}$ was separated on an 8% SDS-PAGE and blotted onto nitrocellulose membranes. PSGL-1/mIgG$_{2b}$, chimeras were probed with an anti-mouse IgG antibody (A), an anti-blood group A antibody followed by a goat anti-mouse IgM antibody (B), an anti-H type 2 chain-specific antibody followed by a goat anti-mouse IgM-HRP antibody (C), and an anti-H type 3 chain-specific antibody followed by an HRP-labeled goat anti-mouse IgM antibody (D). In panels A-D, samples analyzed were from cells transfected with plasmids encoding PSGL-1/mIgG$_{2b}$ and the H gene (lanes 1 and 2), PSGL-1/mIgG$_{2b}$ and the Hand A gene (lanes 3 and 4), PSGL-1/mIgG$_{2b}$ and the Se gene (lanes 5 and 6), or PSGL-1/mIgG$_{2b}$ and the Se and A gene (lanes 7 and 8).
Figure 3:
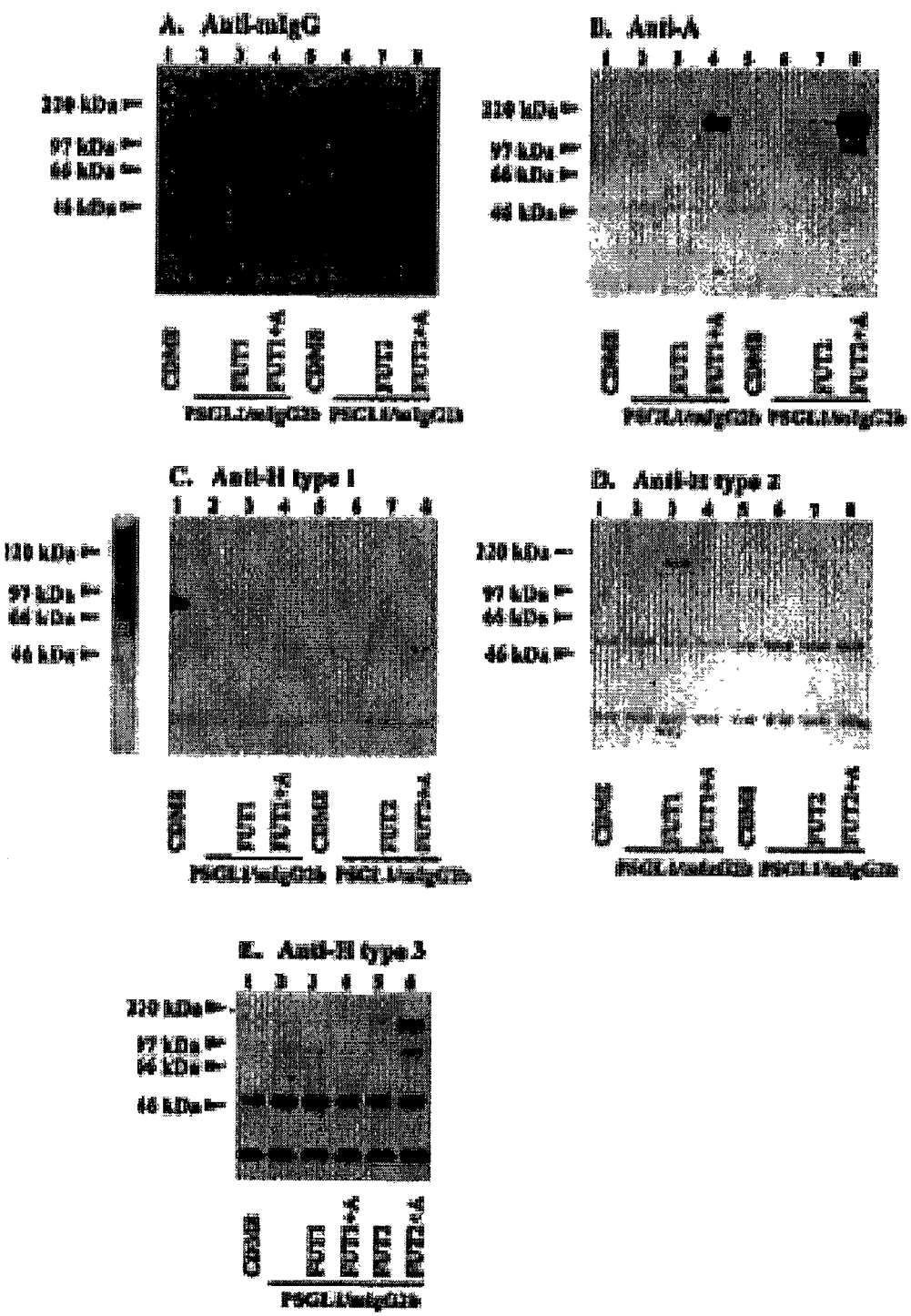
FIGS. 3 A-E are photographs SDS-PAGE and western blot analysis of immunopurified PSGL-1/mIgG$_{2b}$ chimeras produced in COS-7 m6 cells transfected with the H or Se gene alone or in combination with the A gene encoded α1,3 GalNAcT. Following separation on an 8% SDS-PAGE and blotting onto nitrocellulose membranes, the PSGL-1/mIgG$_{2b}$ chimeras were probed with an anti-mouse IgG antibody (A), an anti-blood group A antibody followed by a goat anti-mouse IgM antibody (B), an anti-H type 1 chain-specific antibody followed by an HRP-labeled goat anti-mouse IgG$_3$ antibody (C), an anti-H type 2 chain-specific antibody followed by a goat anti-mouse IgM-HRP antibody (D), and an anti-H type 3 chain-specific antibody followed by a HRP-labeled goat anti-mouse IgM antibody (E). In panels A-D, samples analyzed were from cells transfected with plasmids encoding CDM8 (lanes 1 and 5), PSGL-1/mIgG$_{2b}$ (lanes 2 and 6), PSGL-1/mIgG$_{2b}$, and the H gene (lane 3), PSGL-1/mIgG$_{2b}$ and the H and A gene (lane 4), PSGL-1/mIgG$_{2b}$ and the Se gene (lane 7), or PSGL-1/mIgG$_{2b}$ and the Se and A gene (lane 8). In E the duplicate samples from CDM8 and PSGL1/mIgG$_{2b}$ transfected cells were omitted. In C, 250 ng of H-type 1 chain-BSA was used as a positive control.
Figure 4:
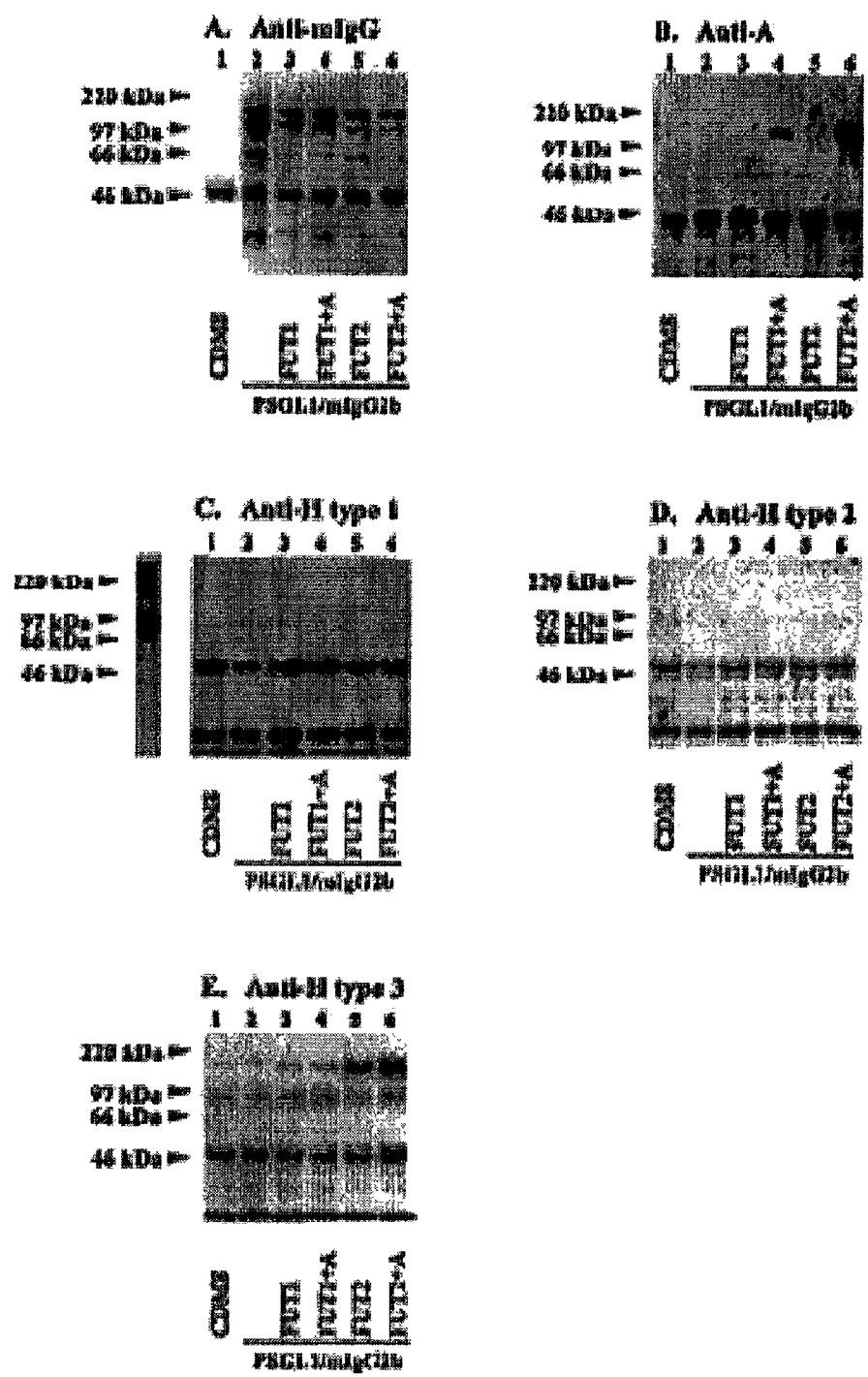
FIGS. 4 A-E are photographs of SDS-PAGE and western blot analysis of immunopurified PSGL-1/mIgG$_{2b}$ chimeras produced in CHO-K1 cells transfected with the H or Se gene alone or in combination with the A gene encoded ∀1,3 GalNAcT. Following separation on an 8% SDS-PAGE and blotting onto nitrocellulose membranes, the PSGL1/mIgG$_{2b}$ chimeras were probed with an anti-mouse IgG antibody (A), an anti-blood group A antibody followed by a goat anti-mouse IgM antibody (B), an anti-H type 1 chain-specific antibody followed by an HRP-labeled goat anti-mouse IgG$_3$ antibody (C), an anti-H type 2 chain-specific antibody followed by a goat anti-mouse IgM-HRP antibody (D), and an anti-H type 3 chain-specific antibody followed by an HRP-labeled goat anti-mouse IgM antibody (E). Samples analyzed were from cells transfected with plasmids encoding CDM8 (lane 1), PSGL-1mIgG$_{2b}$ (lane 2), PSGL-1/mIgG$_{2b}$ and the H gene (lane 3), PSGL-1/mIgG$_{2b}$ and the H and A gene (lane 4), PSGL-1/mIgG$_{2b}$, and the Se gene (lane 5), or PSGL-1/mIgG$_{2b}$ and the Se and A gene (lane 6). In C, 250 ng of H-type 1 chain-BSA was used as a positive control.

Both FUT1 and FUT2 could with the α1,3 GalNAcT support the biosynthesis of blood group A chains on the PSGL-1/mIgG$_{2b}$ (B). The combination of FUT2 and the α1,3 GalNAcT seemed to create more A epitopes on PSGL-1/mIgG$_{2b}$, than the combination of FUT1 and the α1,3 GalNAcT (cf. these lanes in B). On the other hand, FUT1 alone supported expression of abundant H type 2 structures (D), whereas FUT2 gave rise to few H type 2 epitopes on the mucin/Ig (D). There were no detectable H type 1 structures on PSGL-1/mIgG$_{2b}$(C). The H epitopes created by FUT2 were based almost exclusively on type 3, that is, Fucα2Galβ3GalNAcα-R, because no H type 1 structures and few H type 2 structures were made on PSGL-1/mIgG$_{2b}$ by this enzyme (E). Interestingly, cotransfection of both the H or Se gene with the A gene gave rise to abundant epitopes on the PSGL-1/mIgG$_{2b}$ reactive with the anti-H type 3 antibody (E). Blood group A, H type 2 and 3 epitopes were mainly O-linked, because peptide N-glycosidase F (PNGaseF) treatment of PSGL-1/mIgG$_{2b}$, did not decrease antibody staining using antibodies specific for these epitopes (FIGS. 2B-D). Efficient N-glycan deglycosylation was indicated by a complete mobility shift of the PSGL-1/mIgG$_{2b}$ (FIGS. 2A-D).

COS cells. The western blot analysis of PSGL-1/mIgG$_{2b}$ made in COS cells is shown in FIGS. 3A-E. Although weaker, the pattern of PSGL-1/mIgG$_{2b}$ staining using anti-A and H specific antibodies was somewhat similar to that found for the PSGL-1/mIgG$_{2b}$ made in 293T cells. Both FUT1 and FUT2 could together with the α1,3 GalNAcT support A epitope expression, with more epitopes created by FUT2 and the α1,3 GalNAcT (B). Only FUT1 could make H type 2 structures (D), and neither FUT1 nor FUT2 supported expression of H type 1 structures in COS cells (C). In contrast to the PSGL-1/mIgG$_{2b}$ made in 293T-cells, very low levels of H type 3 epitopes were seen on the PSGL-1/mIgG$_{2b}$, produced in COS cells coexpressing FUT1 and the α1,3 GalNAcT, or the FUT2 enzyme alone (E).

However, joint expression of FUT2 and the α1,3 Gal-NAcT gave rise to increased reactivity with the H type 3 antibody (E). Furthermore, weak bands were seen with the anti-A antibody when only the α1,2 FTs were expressed, indicating a weak endogenous activity of an α1,3 GalNAcT in COS cells, as previously reported (Clarke and Watkins, 1999). PNGaseF treatment of PSGL-1/mIgG$_{2b}$ did not show any detectable reduction in anti-blood group A, H type 2 or 3 antibody staining (data not shown), indicating that these epitopes are mainly carried on PSGL-1/mIgG$_{2b}$ O-glycans.

Chinese hamster ovary (CHO) cells. FIGS. 4A-E, shows the staining of PSGL-1/mIgG$_{2b}$ made in CHO cells, PSGL-1/mIgG$_{2b}$ carried blood group A epitopes following coexpression of FUT1 or FUT2 cDNAs with the α1,3 GalNAcT (B). Neither H type 1 (C) nor H type 2 (D) structures could be detected on the PSGL-1/mIgG$_{2b}$ chimera made in CHO cells following cotransfection with either FUT1 or FUT2, suggesting that H type 3 structures are the sole precursors available for the α1,3 GalNAcT. Staining with the anti-H-type 3 antibody was seen with both FUT1 and FUT2 (B), supporting the theory that the A epitopes are based solely on core 1 structures in CHO cells, Further support to this was obtained after PNGaseF treatment, which did not affect the antibody staining intensity, indicating an O-glycan restricted A epitope expression (data not shown). The number of A epitopes and H type 3 epitopes on the PSGL-1/mIgG$_{2b}$ chimera were clearly higher with FUT2 as compared to FUT1 suggesting that the Se gene product is superior to the H gene product in terms of α1,2-fucosylation of core 1 (Galβ3GalNAcα-Ser/Thr) structures.

EXAMPLE 3

Figure 5:
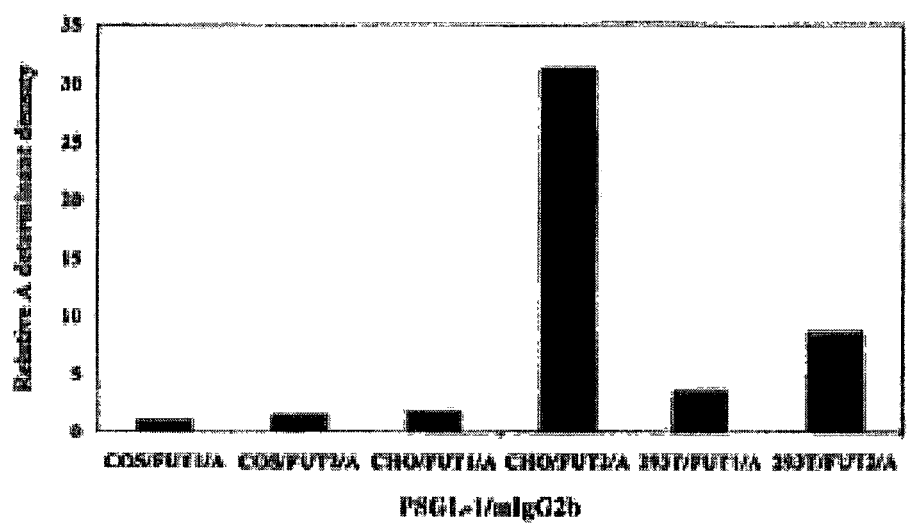
FIG. 5 is a bar graph showing the relative blood group A density on recombinant PSGL-1/mIg$_{2b}$, produced in COS, CHO, and 2931 cells coexpressing FUT1 or FUT2 with α1,3 GalNAcT. The density was calculated as the ratio of the volumes for the blood group A and the mIgG reactivities and the values were normalized to the ones obtained for the A substituted PSGL-1/mIgG$_{2b}$ produced in COS cells coexpressing FUT1 and the α1,3 GalNAcT.

Relative Blood Group A Epitope Density on PSGL-1/mIgG$_{2b}$ Produced in Different Host Cells To semi-quantify the relative number of A epitopes on the PSGL-1/mIgG$_{2b}$ chimera made in various host cells expressing the A gene with either of the α1,2 FTs, western blotting with anti-A antibodies and anti-mIgG antibodies followed by chemiluminescence detection in a Fluor-S®Max MultI-mager was used. The ratios of the blood group A and the mIgG reactivities for each PSGL-1/mIgG$_{2b}$ are shown in FIG. 5 (one of three representative experiments shown). As seen, the A epitope density was highest on the PSGL-1/mIgG$_{2b}$ made in CHO cells expressing the A gene together with the Se gene encoded α1,2 FT. This PSGL-1/mIgG$_{2b}$, carried approximately three times more A epitopes than the PSGL-1/mIgG$_{2b}$, made in 293T cells transfected with FUT2 and the A gene; the PSGL-1/mJgG$_{2b}$, having the second highest A epitope density (FIG. 5). In each cell line, the FUT2 gave higher A epitope density together with the A gene than did FUT1 together with the A gene.

EXAMPLE 4

Figure 6:
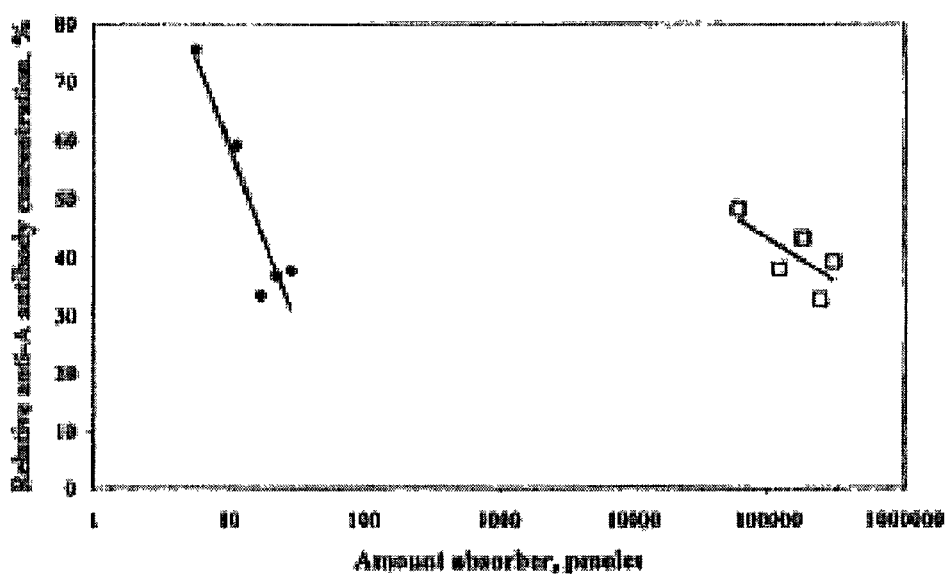
FIG. 6 is a line chart showing Anti-blood group A reactivity remaining in serum after absorption on different blood group A substituted absorbents. The remaining reactivity, in percentage of nonabsorbed blood group O serum, as measured by an ELISA coated with A-PAA-biotin, was plotted against the amount of absorber used. A trend line was calculated using logarithmic regression. The circles represent PSGL-1/mIgG$_{2b}$ produced in CHO cells with FUT2 and α1,3 GalNAcT, and the squares represent A trisaccharides linked via A-PAA-MPG. B trisaccharides coupled via B-PAA-MPG were used to obtain the same amount of PAA-MPG in all absorptions.

Absorption of Anti-A Antibodies on PSGL-1/mIgG$_{2b}$ Carrying Blood Group A Epitopes The efficacy of anti-A antibody absorption on recombinant PSGL-1/mIgG$_{2b}$ with or without blood group A epitopes was compared to that of absorption on A trisaccharides linked via poly[N-(2-hydroxyethyl)acrylamide] to macroporous glass beads (A-PAA-MPG). Pre- and postabsorption anti-A-antibody levels were assessed in an enzyme-linked immunosorbent assay (ELISA) in which the plate was coated with A trisaccharides linked to poly[N-(2 -hydroxyethyl)acrylamide also substituted with biotin (A-PAA-biotin). The results are shown in FIG. 6. Twenty pmoles of recombinant A epitope-substituted PSGL-1/mIgG$_{2b}$, were needed to absorb 60% of the anti-A antibodies as detected in the A-PAA-biotin ELISA, whereas 164,000 pmoles of A determinants as A-PAA-MPG were needed to absorb the same amount of anti-A antibodies. The PSGL-1/mIgG$_{2b}$ dimer has 106 potential O-linked glycosylation sites and eight potential N-linked glycosylation sites (Wilkins et al, 1996; Aeed et al., 1998, 2001), of which the latter eight may carry branched structures. If one assumes that each PSGL-1/mIgG$_{2b}$ carries approximately 100 A epitopes, which most likely is an over-estimation, the mucin made in CHO cells with FUT2 and the α1,3GalNacT is approximately 80 times more efficient on a carbohydrate molar basis than is A-PAAF-MPG.

EXAMPLE 5

Treating or Preventing Antibody Mediated Graft Rejection

Organ transplantation across the ABO barrier is characterized by AMR mediated by preformed or induced antibodies against the donor organ blood group (Porter, 1963; Sanchez-Urdazpal et al., 1993; Farges et al., 1995; Tanabe et al, 1998; Alkhunaizi et al., 1999). Anti-ABO antibodies are removed using a PSGL-1/mIgG$_{2b}$ fusion protein carrying A determinants as the absorber in an EIA setting. Results show that approximately 20 pmoles of recombinant PSGL-1/mIgG$_{2b}$ (calculated on a molecular weight of 300 kDa), corresponding to 2 nmoles of A determinants (based on 100 A determinants per mole of PSGL-1/mIgG$_{2b}$) (Wilkins et al., 1996; Aeed et al., 1998, 2001) made in CHO-K1 with FUT2 and α1,3 GalNAcT could absorb 60% of the A-PAA-reactive antibodies. A-PAA-MPG corresponding to approximately 164,000 pmoles of A trisaccharides (calculated on 2 μmol/μg) was needed to absorb the same amount of anti-A antibodies. The amount of nonspecific protein absorption for both compounds was also assessed, and the nonspecific absorption was almost fourfold higher with the PAA-MPG-based compounds. The relatively higher absorption efficacy of mucin-based absorbers may depend on (1) multivalent carbohydrate substitution, (2) close spacing of carbohydrate epitopes, and (3) a structural versatility of the core saccharide chains that carry the immunodominant determinant. Furthermore, changing the protein backbone, for example, by making a synthetic mucin-type protein constructed by optimized mucin tandem repeats, may improve the absorber (Silverman et al., 2001). Also, cells engineered to express different combinations of GalNAc:polypeptide transferases may improve absorption efficacy by optimising the O-glycan substitution density.

ABBREVIATIONS

AMR, antibody-mediated rejection; BSA, bovine serum albumin; CHO, Chinese hamster ovary; COS, ETA, extracorporeal immunoabsorption; ELISA, enzyme-linked immunosorbent assay; FT, fucosyltransferase; GalNAcT, N-acetylgalactosaminyltransferase; HRP, horseradish peroxidase; mIgG, mouse IgG; mIgM, mouse 1 gM; MPG, macroporous glass beads; PAA, poly[N-(2-hydroxyethyl)

acrylamide]; PBS, phosphate buffered saline; PBS-T, PBS with 0.05% Tween; PCR, polymerase chain reaction; PNGaseF, peptide:N-glycosidase F; PP, plasmapheresis; PSGL-1, P-selectin glycoprotein ligand-1; SDS-PAGE, sodium dodecyl sulfate-polyacrylamide gel electrophoresis; TBS-T, Tris-buffered saline with 0.05% Tween-20; Tx, transplantation.

REFERENCES

Aeed, P A., Geng, J. G., Asa, D., Raycroft, L., Ma, L., and Elhammer, A. P. (1998) Characterization of the 0-linked oligosaccharide structures on P-selectin glycoprotein ligand-1 (PSGL-1). *Glycoconj. J.*, 15,975.

Aeed, P. A., Geng, 3.0., Asa, D., Raycroft, L., Ma, L., and Elhammer, A. P. (2001) Partial characterization of the N-linked oligosaccharide structures on P-selectin glycoprotein ligand-1 (PSGL-1), *Cell, Res.*, 11, 28.

Alkhunaizi, A M., de Mattos, A. M., Bariy, J. M., Bennett, W. M., and Noiman, D. J. (1999) Renal transplantation across the ABO barrier using A2 kidneys. *Transplantation*, 67, 1319.

Benjamin, R. J. and Antin, J. H. (1999) ABO-incompatible bone marrow transplantation: the transfusion of incompatible plasma may exacerbate regimen-related toxicity. *Transfusion*, 39, 1273.

Benjamin, R J., McGurk, S., Ralston, M. S., Churchill, W. H., and Antin, J. H. (1999) ABO incompatibility as an adverse risk factor for survival after allogeneic bone marrow transplantation. *Transfusion*, 39, 179.

Bensinger, W I. (1981) Plasma exchange and immunoadsorption for removal of antibodies prior to ABO incompatible bone marrow transplant. *Artif Organs*, 5,254.

Bensinger, W. I., Baker, D. A., Buckner, C. D., Clift, R. A., and Thomas, E. D. (1981a) Immunoadsorption for removal of A and B blood-group antibodies. *N. Engl. J. Med.*, 304, 160.

Bensinger, W I., Baker, D. A., Buckner, C. D., Clift, R. A., and Thomas, E. D. (1981b) In vitro and in vivo removal of anti-A erythrocyte antibody by adsorption to a synthetic immunoadsorbent. *Transfusion*, 21, 335.

Bensinger, W. I., Buckner, C D., Baker, D. A., Clift, R. A., and Thomas, E. D. (1982) Removal of specific antibody in vivo by whole blood immunoadsorption: preliminary results in dogs.). *J. Clin. Apheresis.*, 1,2.

Bensinger, W I., Buckner, C D., Clift, R. A., and Thomas, E D. (1987) Plasma exchange and plasma modification for the mmoval of anti-red cell antibodies prior to ABO-incompatible marrow transplant.). *J. Clin. Apheresis.*, 3, 174.

Betteridge, A. and Watkins, W, M. (1985) Variant forms of alphal, 2fucosyltransferase in human submaxillary glands from blood group ABH "secretor" and "non-secretor" individuals. *Glycoconj. J.*, 2,61.

Beyer, T. A., Sadler, J. E. and Hill, R. L. (1980) Purification to homogeneity of H blood group beta-galactoside alpha 1 leads to 2 fucosyltransferase from porcine submaxillary gland.). *J. Biol. Chem.*, 255, 5364.

Carraway, K. L. and Hull, S. R. (1991) Cell surface mucin-type glycoproteins and mucin-like domains. *Glycobiology*, 1, 131.

Clarke, J. L. and Watkins, W. M. (1999) Expression of human alpha-1-fucosyl-transferase gene homologs in monkey kidney COS cells and modification of potential fucosyltransferase acceptor substrates by an endogenous glycosidase. *Glycobiology*, 9, 191.

Clausen, H. and Hakomori, S. (1989) ABH and related histo-blood group antigens; immunochemical differences in carrier isotypes and their distribution. *Vox. Sang.*, 56, 1.

Cooper, D. K., Ye, Y., Niekrasz, M., Kehoe, M., Martin, M., Neethling, F. A., Kosanke, S., DeBault, L. E., Worsley, G, Zuhdi, N., and others. (1993) Specific intravenous carbohydrate therapy. A new concept in inhibiting antibody-mediated rejection-experience with ABO-incompatible cardiac allografting in the baboon. *Transplantation*, 56, 769.

Donald, A. S. (1981) A-active trisaccharides isolated from A1 and A2 blood-group-specific glycoproteins. *Eur. J Biochem.*, 120, 243, Eid, A., Zamir, G., Yaron, I., Galun, E., Safadi, R., Schaaps, 1., Berlatzky, V., Shouval, D., and iurim, 0. (1998) Liver transplantation across the ABO barrier: the role of plasmapheresis. *Transplant Proc.*, 30, 701.

Ernst, L. K., Rajan, V. P., Larsen, RD., Ruff, M. M., and Lowe, J, B. (1989) Stable expression of blood group H determinants and GDP-L-fucose: betaD-galactoside 2-alpha-L-fucosyltransferase in mouse cells after transfection with human DNA. *J. Biol. Chem.*, 264, 3436.

Fargea, O., Kalil, A. N., Samuel, D., Saliba, F, Anjlnaden, i. L., Debat, P., Bismuth, A., Castaing, D., and Bismuth, H. (1995) The use of ABO-incompatible grafts in liver transplantation: a life-saving procedure in highly selected patients. *Transplantation*, 59, 1124, Gale, R. P., Feig, S., Ho, W., Falk, P., Rippee, C., and Sparkes, R. (1977) ABO blood group system and bone marrow transplantation. *Blood*, 50, 185.

Galili, U. and Matta, K. L. (1996) Inhibition of anti-Gal IgG binding to porcine endothelial cells by synthetic oligosaccharides. *Transplantation*, 62, 256.

Gibbons, R D., Meltzer, D., and Duan, N. (2000) Waiting for organ transplantation. Institute of Medicine Committee on Organ Transplantation. *Science*, 287, 237.

Gugenheim, J., Samuel, D., Reynes, M., and Bismuth, H. (1990) Liver transplantation across A130 blood group barriers. *Lancet*, 336, 519.

Hakomori, S. (1999) Antigen structure and genetic basis of histo-blood groups A, B and 0: their changes associated with human cancer. *Biochim. Biophys. Acta*, 1473, 247.

Holgersson, J, Breimer, M. E., and Samuelsson, B. E. (1992) Basic biochemistry of cell surface carbohydrates and aspects of the tissue distribution of histo-blood group ABH and related glycosphingolipids. *APMiS Suppl.*, 27, 18.

Ishikawa, A., Itoh, M., Ushlyama, T., Suzuki, K., and Fujita, K. (1998) Experience of ABO-incompatible living kidney transplantation after double filtration plasinapheresis. *Clin. Transplant.*, 12, 80.

Kelly, Ri., Rouquier, S., Giorgi, D., Lennon, G. G., and Lowe, J. B (1995) Sequence and expression of a candidate for, the human Secretor blood group alpha(1, 2)fucosyltransferase gene (FUT2). Homozygosity for an enzyme-inactivating nonsense mutation commonly correlates with the non-secretor phenotype.). *Biol. Chem.*, 270,4640.

Kumazaki, T. and Yoshida, A. (1984) Biochemical evidence that secretor gene, Se, is a structural gene encoding a specific fucosyltransferase. *Proc. Natl. Acad. Sci. USA*, 81,4193.

Kyprianou, P., Betteridge, A., Donald, A. S., and Watkins, W. M. (1990) Purification of the blood group Hgeneassociatedalpha-2-L-fucosyltransferase from human plasma. *Glycoconj. J*, 7, 573.

Laemmli, U. K. (1970) Cleavage of structural proteins during the assembly of the head of bacteriophage 14. *Nature*, 227, 680.

Larsen, R, D., Ernst, L. K., Nair, R. P., and Lowe, J. B. (1990) Molecular cloning, sequence, and expression of a human GDP-L-fucose:beta-D-galactoside 2-alpha-L-fucosyltransferase cDNA that can form the H blood group antigen. *Proc. Nail Acad. Sci. USA,* 87,6674.

Le Pendu, I., Cartron, J. P., Lemieux, R. U., and Oriol, R. (1985) The presence of at least two different H-blood-group-related beta-D-gal alpha-2-L-fuco-syltransferases in human serum and the genetics of blood group H substances. *Am. J. Hum. Genet.,* 37,749.

Liu, J., Qian, Y., and Holgersson, 1. (1997) Removal of xenoreactive human anti-pig antibodies by absorption on recombinant mucin-containing glycoproteins carrying the Gal alphal, 3Gal epitope. *Transplantation,* 63, 1673.

Liu, Y., Fujitani, N., Koda, V., Soejima, M., and Kimura, H. (1999) Presence of H type ¾ chains of ABO histo-bbood group system in serous cells of human submandibular gland and regulation of their expression by the secretor gene (FUT2) *J. Histochem. Cytochem.,* 47,889, Liu, V. H., Fujitani, N., Koda, V., and Kimura, H. (1998) Distribution of H type 1 and of H type 2 antigens of ABO blood group in different cells of human submandibular gland.). *J. Histochem. Cytochem.,* 46, 69.

Lowe, I. B. (1999) Structures common to different types of glycans. In Varki, A., Cummings, R., Esko, J., Freeze, H., Hart, G., and Marth, J., eds., *Essentials of Glycobiology.* Cold Spring Harbor Laboratory Press, Cold Spring Harbor, N.Y., 21 1-252.

Porter, K. A. (1963) Morphological aspects of renal homograft rejection. *Br. Med. Bull.,* 21, 171.

Prieto, P. A., Larsen, RD., Cho, M., Rivera, H. N., Shilatifard, A., Lowe, J. B., Cummings, R D., and Smith, D. F. (1997) Expression of human H-type alphal, 2-fucosyltransferase encoding for blood group H(0) antigen in Chinese hamster ovary cells. Evidence for preferential fucosylation and truncation of polylactosamine sequences.). *J. Biol. Chem.,* 272, 2089.

Prieto, P. A., Mukerji, P., Kelder, B., Emey, R., Gonzalez, D., Yun, J S., Smith, D. F., Moremen, K. W., Nardelli, C., Pierce, M., and others. (1995) Remodeling of mouse milk glycoconjugates by transgenic expression of a human glycosyltransferase. *J. Biol. Chem.,* 270, 29515.

Rajan, V. P., Larsen, R D., Ajmera, S., Ernst, L. K., and Lowe, J. B. (1989)A cloned human DNA restriction fragment determines expression of a GDP-L-fucose: beta-D-galactoside 2 -alpha-L-fucosyltransferase in transfected cells. Evidence for isolation and transfer of the human H blood group locus. *J. Biol. Chem.,* 264, 11158.

Rieben, R., Korchagina, E. Y., von Allmen, E., Hovinga, i. K., Lammle, B., iungi, T. W., Bovin, N. y., and Nydegger, U. E. (1995) In vitro evaluation of the efficacy and biocompatibility of new, synthetic ABO immunoabsorbents. *Transplantation,* 60,425.

Rouquier, S., Lowe, J. B., Kelly, Ri. Fertitta, A L., Lennon, G. G., and Giorgi. D. (1995) Molecular cloning of a human genomic region containing the H blood group alpha(1, 2)fucosyltransferase gene and two H locus-related DNA restriction fragments. Isolation of a candidate for the human Secretor blood group locus.). *J. Biol. Chem.,* 270, 4632.

Sanchez-Urdazpal, L., Batts, K, P., Gores, G. i., Moore, S. B., Sterioft, S., Wiesner, R. H., and Krom, R. A. (1993) Increased bile duct complications in liver transplantation across the ABO barrier. *Ann. Surg.,* 218, 152.

Samesto, A., Kohlin, 1, Hindsgaul, 0., Thurin, J., and Blaszczyk-Thurin, M. (1992) Purification of the secretor-type beta-galactoside alpha 1-2-fucosyltransferase from human serum.). *J. Biol. Chem.,* 267, 2737.

Sarnesto, A., Kohlin, T., Thurin, i., and Blaszczyk-Thurin, M. (1990) Purification of H gene-encoded beta-galactoside alpha 1-2 fucosyltransferase from human serum. *J. Biol. Chem.,* 265, 15067.

Seed, B. (1987) An LFA-3 cDNA encodes a phospholipid-linked membrane protein homologous to its receptor CD2. *Nature,* 329, 840.

Shimizu, V. and Shaw, S. (1993) Cell adhesion. Mucins in the mainstream. *Nature,* 366,630.

Silverman, H. S., Parry, S., Sutton-Smith, M., Burdick, M. D., McDermott, K., Reid, C. J., Batra, S. K., Morris, H. R., Hollingsworth, M. A., Dell, A., and Harris, A. (2001) In vivo glycosylation of mucin tandem repeais. *Glycobiology,* 11,459.

Simon, P. M., Neethling, F. A., Taniguchi, S., Goode, P. L, Zopf, D., Hancock, W. W., and Cooper, D. K. (1998) Intravenous infusion of Galalphal-3Gal oligosaccharides in baboons delays hyperacute rejection of porcine heart xenografts. *Transplantation,* 65, 346.

Takasaki, S., Yamashita, K., and Kobata, A. (1978) The sugar chain structures of ABO blood group active glycoproteins obtained from human erythrocyte membraned. *J. Biol. Chem.,* 253,6086.

Tamaki, T., Tanaka, M., Katori, M., Osanai, M., Yasuhara, M., Meguro, i., Kukita, K., Yonekawa, M., and Kawamura, A. (1998) Cryofiltration apheresis for major ABO-incompatible kidney transplantation. *Ther, Apher.,* 2,308.

Tanabe, K., Takahashi, K., Sonda, K., Tokumoto, 1., Ishikawa, N., Kawai, T., Fuchinoue, S., Oshima, 1., Yagisawa, 1., Nakazawa, H., and others. (1998) Long-term results of ABO-incompatible living kidney transplantation: a single-center experience. *Transplantation,* 65, 224.

Wilkins, P P., McEver, R. P., and Cummings, R D. (1996) Structures of the 0-glycans on P-selectin glycoprotein ligand-! from HL-60 cells. *J. Biol. Chem.,* 271, 18732.

Yamamoto, F., Clausen, H., White, 1., Marken, J., and Hakomori, S. (1990) Molecular genetic basis of the histo-blood group ABO system. *Nature,* 345, 229.

Ye, V., Niekrasz, M., Kehoe, M., Rolf, L. L. Jr., Martin, M., Baker, J., Kosanke, S., Romano, E., Zuhdi, N., and Cooper, D. K. (1994) Cardiac allotransplantation across the ABO-blood group barrier by the neutralization of preformed antibodies: the baboon as a model for the human. *Lab. Aniim. Sci.,* 44,121.

Yeh, J. C., Hiraoka, N., Petryniak, B., Nakayama, J., Ellies, L. G., Rabuka, D., Hindsgaul, O., Marth, I D., Lowe, i. B., and Fukuda, M. (2001) Novel sulfated lymphocyte homing receptors and their control by a core 1 extension beta I, 3-N-acetylglucosaminyltransferase. *Cell,* 105, 957.

Zerfaoui, M., Fukuda, M., Sbarra, V., Lombardo, D., and El-Battari, A. (2000) Alpha(1, 2)-fucosylation prevents sialyl Lewis x expression and Eselectin-mediated adhesion of fucosyltransferase VII-transfected cells. *Eur. J. Biochem.,* 267,53.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion polypeptide comprising a first polypeptide operably linked to a second polypeptide, wherein the first polypeptide:
   (a) is a mucin polypeptide and
   (b) is glycosylated by an α1,2 fucosyltransferase and the second polypeptide comprises at least a region of an immunoglobulin polypeptide.

2. The fusion polypeptide of claim 1, wherein the first polypeptide glycosylated by the α1,2 fucosyltransferase is further glycosylated by an α1,3 N-acetylgalactosaminyltransferase or an α1,3 galactosyltransferase.

3. The fusion polypeptide of claim 1, wherein the α1,2 fucosyltransferase is a blood group H or Secretor α1,2 fucosyltransferase.

4. The fusion polypeptide of claim 1, wherein the first polypeptide comprises at least a region of a P-selectin glycoprotein ligand-1.

5. The fusion polypeptide of claim 4, wherein said first polypeptide includes an extracellular portion of a P-selectin glycoprotein ligand-1.

6. The fusion polypeptide of claim 1, wherein the second polypeptide comprises a region of a heavy chain immunoglobulin polypeptide.

7. The fusion polypeptide of claim 6, wherein said second polypeptide comprises an Fc region of an immunoglobulin heavy chain.

8. The fusion polypeptide of claim 1, wherein the fusion polypeptide is a dimer.

* * * * *